US011055386B2

(12) United States Patent
Mueglitz et al.

(10) Patent No.: US 11,055,386 B2
(45) Date of Patent: Jul. 6, 2021

(54) CONTROLLING USER ACCESS TO A MEDICAL SYSTEM

(71) Applicant: Roche Diabetes Care, Inc., Indianapolis, IN (US)

(72) Inventors: Carsten Mueglitz, Schoenau (DE); Nils Danckwardt, Tübingen (DE); Andreas Huber-Toth, Innsbruck (AT); Simon Wetzel, Leinfelden-Echterdingen (DE); Andreas Seidel, Edingen-Neckarhausen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/563,705

(22) Filed: Sep. 6, 2019

(65) Prior Publication Data
US 2019/0392124 A1 Dec. 26, 2019

Related U.S. Application Data

(63) Continuation of application No. PCT/EP2018/055051, filed on Mar. 1, 2018.

(30) Foreign Application Priority Data

Mar. 9, 2017 (EP) .................................. 17160137

(51) Int. Cl.
G06F 21/00 (2013.01)
G06F 21/31 (2013.01)
(Continued)

(52) U.S. Cl.
CPC ............ *G06F 21/31* (2013.01); *G16H 20/17* (2018.01); *G16H 40/67* (2018.01); *H04W 12/08* (2013.01);
(Continued)

(58) Field of Classification Search
CPC . G06F 21/31; H04W 12/08; H04W 12/00504; H04W 12/00512;
(Continued)

(56) References Cited

U.S. PATENT DOCUMENTS 8,364,231 B2 * 1/2013 Kamath ............... A61B 5/1495
600/347
10,166,333 B2 * 1/2019 Friedli .................. G16H 40/67
(Continued)

FOREIGN PATENT DOCUMENTS

EP    1 631 939 B1    6/2019

OTHER PUBLICATIONS

International Search Report and Written Opinion of the International Searching Authority, PCT/EP2018/055051, dated May 14, 2018, 15 pages.
(Continued)

*Primary Examiner* — Mahfuzur Rahman
(74) *Attorney, Agent, or Firm* — Bose McKinney & Evans LLP

(57) ABSTRACT

Disclosed is a method for controlling user access to a medical system including a body-wearable medical device that can be, e.g., an insulin pump and/or a continuous glucose monitor. A remote controller is provided and has a user interface and can exchange data with the medical device. The remote controller is configured for entering, via the user interface, at least one command for execution by the medical device. The remote controller has a locked state in which entering medical device commands or other commands is disabled. In the locked state, the user is prompted to enter an identification code and the remote controller can be unlocked when the correct identification code is entered. In the unlocked state, entering of the medical device command is enabled. Alternatively, instead of entering a correct
(Continued)

identification code, the remote controller can be switched to the unlocked state when a safety condition is met.

15 Claims, 5 Drawing Sheets

(51) Int. Cl.
    *G16H 20/17*     (2018.01)
    *G16H 40/67*     (2018.01)
    *H04W 12/08*     (2021.01)
    *H04W 12/65*     (2021.01)
    *H04W 12/71*     (2021.01)
    *H04W 12/77*     (2021.01)

(52) U.S. Cl.
    CPC ............ *H04W 12/65* (2021.01); *H04W 12/71* (2021.01); *H04W 12/77* (2021.01)

(58) Field of Classification Search
    CPC . H04W 12/00522; G16H 20/17; G16H 40/67; G08C 2201/91
    See application file for complete search history.

(56) References Cited

U.S. PATENT DOCUMENTS

| | | |
|---|---|---|
| 2006/0132283 A1 | 6/2006 | Eberhart et al. |
| 2008/0125064 A1 | 5/2008 | Das et al. |
| 2015/0018633 A1* | 1/2015 | Kovachev ............ A61B 5/0022 600/301 |
| 2015/0207626 A1 | 7/2015 | Neftel et al. |
| 2017/0173262 A1* | 6/2017 | Veltz ...................... G16H 20/17 |
| 2017/0290980 A1* | 10/2017 | Friedli .................. G16H 40/67 |
| 2017/0347936 A1* | 12/2017 | Stahmann .......... A61B 5/14507 |

OTHER PUBLICATIONS

Rasmussen et al., Proximity-based Access Control for Implantable Medical Devices, Computer and Communications Security, Nov. 9, 2009, pp. 410-419, New York, U.S.

* cited by examiner

CONTROLLING USER ACCESS TO A MEDICAL SYSTEM

RELATED APPLICATIONS

This application is a continuation of PCT/EP2018/055051, filed Mar. 1, 2018, which claims priority to EP 17 160 137.0, filed Mar. 9, 2017, the entire disclosures of each of which are hereby incorporated herein by reference.

BACKGROUND

The present disclosure relates to the field of medical systems, in particular medical systems with an insulin infusion pumps and/or a continuous glucose measurement device. The disclosure further relates to field of controlling user access to such devices.

In the therapy of diabetes mellitus, Continuous Subcutaneous Insulin Infusion (CSII) with an insulin infusion pump is used in increasing numbers. Such insulin infusion pumps are typically designed as computer-controlled high-precision metering pumps that are carried by a Person with Diabetes (PwD) substantially continuously and administer insulin in a substantially continuous according to a typically time-varying basal infusion schedule. Further, they are designed to administer insulin bolus of desired size on demand.

Continuous glucose measurement devices are used in increasing numbers and are also designed to be carried substantially continuously and provide substantially continuous glucose level information. Both an insulin infusion pump and a continuous blood glucose measurement device may be used alone or in combination. In a medical system that comprises both an insulin infusion pump and a continuous blood glucose measurement device, these components may be operatively coupled, thereby providing a user assistance in controlling and/or adjusting the insulin administration and/or automatically controlling the insulin administration based on the measured glucose data according to a fully or partly closed control loop.

Insulin infusion pumps and/or continuous glucose measurement devices are commercially available from a number of supplier, such as Roche Diabetes Care GmbH, Germany; Medtronic Minimed Inc, CA, USA; Dexcom, Inc, CA, USA.

SUMMARY

This disclosure is based on a medical device that includes an insulin infusion pump and/or a continuous glucose measurement device as explained before. An insulin infusion pump may especially be designed for bolus and basal insulin administration as explained.

Due to the increasing demand for both convenience and discreetness, medical devices are increasingly controlled via a remote controller. The combination of a medical device of the above-described type, in particular an insulin infusion pump and/or continuous glucose measurement device and an associated remote controller, is in this document referred to as "medical system."

The remote controller may be a hand-held dedicated device or a general-purpose device such as a cell phone/smart phone, running a corresponding application. In some embodiments, the remote controller provides, in addition to remote control of the insulin infusion pump and/or the continuous blood glucose measurement device, further dedicated functionality such a test-strip based blood glucose meter, a food/carbohydrate database and/or a bolus calculator.

For safety and regulatory reasons, access to programming, altering or generally manipulating medically relevant functions and operations of the medical device needs to be restricted to an authorized user. In this context, it is to be noted that the remote controller may, in contrast to the medical device, be easily lost, stolen etc. and accordingly be in control of a person different from the authorized user. Further regarding insulin infusion pumps it is to be understood that insulin is a highly critical drug. Significant over or under dosing, resulting from an unauthorized manipulation, may result in severe and potentially lethal complications. Regarding continuous glucose measurement devices, the same applies in principle if they are directly operatively coupled with the insulin infusion pump as closed control loop. Even if this is not the case, improper and unauthorized user commands may result in significantly incorrect measurement results and therefore cause inappropriate therapeutically measures.

For restricting user access to critical medical device commands via the remote controller to an authorized user, a PIN code or the like may be used. Such pin code or authentication code, however, may be temporarily or permanently forgotten.

This disclosure teaches an improvement to the situation regarding the control of user access and in particular in case of a forgotten authentication code, without requiring help or measures to be taken from a further party, such as a hotline.

According to one aspect, this disclosure teaches a method for controlling user access to a medical system. The medical system includes a medical device and remote controller. The method includes:

a) providing the medical device as an extracorporeal body-wearable device including an insulin infusion pump and/or a continuous glucose measurement device, the medical device further comprising a medical device communication unit;

b) providing the remote controller as separate device from the medical device, the remote controller comprising a remote controller user interface and a remote controller communication unit.

The remote controller is designed for entering, via the remote controller user interface, at least one medical device command for execution by the medical device. The medical device communication unit and the remote controller communication unit are adapted for exchange. Typically, the data exchange is wireless, which, however, is not essential.

The method further includes:

c) controlling the remote controller to be in a locked state, wherein, in the locked state, entering of the at least one medical device command and execution of a further command is disabled.

The method further includes, in the locked state:

d) requesting the entry of an identification code via the remote controller user interface and switching, upon correct entry of the identification code, the remote controller into an unlocked state, wherein, in the unlocked state, entering of the at least one medical device command is enabled.

The method further includes, alternatively to step (d):

e) determining by the medical system, whether a safety condition is met, and executing, if the safety condition is met, the further command.

Accessing various functions of the medical device, in particular to the at least one medical device command by entering an identification code according to step (c), is the usual and default way of operation, comparable to the entry of a PIN (Personal Identification Number) as generally known. The personal identification code may, for example, a numeric or alpha-numeric code that is entered via the user interface.

In an embodiment, correct entry of the identification code provides access to all functionality that can be carried out by the medical device upon a corresponding user command. The at least one medical device command may especially be or include medically and in particular therapeutically relevant commands.

If the medical device is or includes an insulin infusion pump, the at least one medical device command may, by way of example, especially include one or more of: commanding the administration of an insulin bolus; changing or re-programming a basal insulin infusion schedule; temporarily adjusting the basal insulin infusion schedule; changing and/or initializing a new insulin cartridge; priming an infusion set; altering system settings, such as the insulin type/concentration and/or time/date settings.

If the medical device is or includes a continuous glucose measurement device, the at least one medical device command may, by way of example, especially include one or more of: inputting sensor calibration data; initializing a new subcutaneous glucose sensor; altering system settings, such as warning or alerting glucose levels and/or time/date settings.

In an embodiment, unlocking the medical device by entering the identification code is generally required for accessing all medical device commands which accordingly belong to the at least one medical device command, with exception of the further command as explained further below. In alternative embodiment, however, medically uncritical commands such as reviewing a history of past insulin infusion for an insulin infusion pump and/or displaying the measured past course of the glucose concentration for a glucose measurement device, may also be accessed in the locked state.

Upon switching the medical device into the unlocked state, all medical device commands that are expected to be executed upon a corresponding command of the user are accessible. In an embodiment, the method further includes, following the entry of the at least one medical device command and/or a pre-defined time after the execution of the at least one medical device command and/or a pre-defined time after switching into the unlocked state, switching the medical device into the locked state again. In an embodiment, the medical device may further be locked upon entry of a dedicated locking command at the remote controller and/or the medical device.

The further command to which access is provided or which is executed in step (e) provides an alternative route for allowing fully or partly controlling the medical system without the safety code being available.

Determining whether the safety condition is met is associated with determining whether the medical system is under control of the authorized user. In this context, it is particularly noted that the remote controller, being a general-purpose device such as a cell phone/smart phone or a dedicated remote controller, is comparatively easy to be stolen, forgotten, lost, or the like and accordingly be operated by an unauthorized person. The medical device, in contrast, is generally carried by a Person with Diabetes (PwD) as authorized user substantially continuously and is directly attached to the body or is in close proximity to the body and connected to the body, e.g., via a catheter. It is accordingly reasonable to assume that the medical device as such is under continuous control of the authorized user.

In an embodiment, the method includes, alternatively to the entry of the identification code in step (d), receiving a user input indicative of the identification code being unavailable, and carrying out step (e) in this case.

In an embodiment, the further command includes switching the medical device into the unlocked state. For this type of embodiment, step (e) provides full access to the functionality of the medical device and in particular to the medical device command. An alternative access method is accordingly provided that may be used alternatively to the entry of the identification code.

In an embodiment, the further command is an altering of the identification code and/or resetting of the remote controller to factory settings. For this type of embodiment, executing step (e) does not generally involve a switching to the unlocked state and does accordingly not allow the at least one medical device command to be executed, but is restricted to operations that may be reasonably carried out in case of a forgotten/lost identification code.

In an embodiment, step (e) includes requesting the input of a further identification code and determining whether the safety condition is met includes determining whether the further identification code is inputted correctly. In an embodiment, the further identification code is provided on or by the remote controller. In an embodiment, the further identification code may be inputted by entering it via the user interface of the remote controller. The further identification code may, for example, be provided on a housing of the medical device and/or the remote controller. The further identification code is an identification code. While it may and typically is not particularly hidden, it is not labelled or otherwise identified as such. By way of example, the further identification code may be a remote controller serial number, a medical device serial number, or a code derived thereof, such as: a code obtained by combining certain digits/characters of a serial number, reversing the order of digits/characters of a serial number, or carrying out a pre-defined mathematical operation on a serial number. While the additional information that is required for correctly determining and entering the further identification code is known to the authorized user (and may be explained, for example, in the instruction manual and/or as part of a user training), it is generally not available to unauthorized users. Similar to a serial number, other information that is generally provided on the medical device and/or the remote controller, such as a manufacturing date, may be used for the same purpose. In some embodiments, the further identification code may consist or be derived from information that is partly present on the medical device and partly on the remote controller, for example the medical device serial number and the remote controller serial number.

In an alternative embodiment that includes the entry of a further identification code, the method may include entering the further identification code via a user interface of the medical device. The method may further includes determining, by the medical device, whether the further identification code is entered correctly and transmitting, in the affirmative case, a corresponding acknowledgement signal to the remote controller. The remote control, upon reception of the acknowledgement signal, carries out the further command. In a variant, the information that is entered by the user as further identification code is transmitted to the remote controller and the remote controller determines whether the further identification code is entered correctly.

Generally, embodiments that rely on information that is present on the medical device and/or require a user input on the medical device provide a particularly high safety level because the medical device is generally under direct control of the authorized user, as explained before.

In an embodiment, the remote controller includes a remote controller sensor and determining whether the safety condition is met includes determining whether the further identification code is recognized by the remote controller sensor. The remote controller sensor may in particular be an optical sensor, such as a camera. For this case of a camera as remote controller sensor, the further information code should be provided in a form that is accessible to the camera. By way of example, it may be provided on a removable housing element, such as a battery compartment cover, that may be temporarily removed from the battery compartment for reading by the camera, without affecting the operation of the remote controller. The further identification code may for example be provided as numerical or alphanumerical code as explained before and the method may include carrying out an OCR (Optical Character Recognition) step. Alternatively or additionally, the further identification code may be a dedicated machine-readable code, such as a bar code or 2-dimensional bar code (e.g., QR-code, DataMatrix code, MaxiCode), or the like.

In an embodiment, the further identification code is provided on or by the medical device. An example for this type of embodiment is the use of a medical device serial number, medical device manufacture date or any other information that is present on the medical device housing.

In further embodiments, the further identification code is provided by way of an output that is generated by the medical device. By way of example, the further identification code may be outputted on a display of the medical device for example as numeric or alpha numeric code, or as one- or two-dimensional bar code. In additional to the increased safety level that results from the required presence of the medical device as explained before, providing the further identification code on or by the medical device is particularly advantageous in the context of embodiments where the further identification code is entered into the remote controller via a remote controller sensor, in particular a camera. Here it is favorable that the medical device is generally accessible and a corresponding portion of the medical device that shows the further identification code (e.g., a display or part of the housing that carries the medical device serial number) may be easily be positioned with respect to the camera as required.

In a further embodiment, the further identification code is provided by way of an acoustic output that is generated by an acoustic output device of the medical device, for example a loudspeaker or buzzer. In such embodiment, the remote controller sensor may be a microphone and the method may include receiving by the microphone the acoustical output and determining whether it corresponds to the further identification code. The acoustic output may be generated, e.g., as tone sequence of varying frequency or as tone sequence of varying tone duration, like a Morse code.

Generally, a further identification code that is generated and provided by the medical device may be pre-determined and static, such as a serial number, or may not be pre-determined. By way of example, the medical device may store as series of further identification codes that are used, if required, one after the other in sequence, or the method may include determining the further identification code by random, e.g., as random numeric or alphanumeric code.

In an embodiment, the method includes transmitting information indicative of the further identification code from the medical device to the remote controller via the medical device communication unit and the remote controller communication unit. Transmitting information indicative of the further identification code via the medical device communication unit and the remote controller communication unit is generally favorable in embodiments where the further identification code is provided on or by the medical device in a non-static way and is inputted into the remote controller as explained before. Transmitting information indicative of the further identification code in this way allows the remote controller to determine whether the further identification code is inputted correctly, in particular by entering via the remote controller user interface or as recognized by the remote controller sensor.

In an embodiment, the further identification code is or is derived from a time-dependent status of the medical device. Information derived from a time-dependent status is a particular example of a non-static and not pre-known further identification code. The time-dependent status may be any information that changes over the application time and is stored and/or can be computed by the medical device.

In an embodiment, the medical device includes an insulin infusion pump and the time-dependent status is determined by past insulin infusion by the medical device. The past insulin infusion may, by way of example, be the amount of bolus insulin that has been infused on demand within a given time span, such as the current day; the total combined basal and bolus insulin amount that that has been infused within a given time span; the amount and/or time of the last insulin bolus; the total amount insulin that has been infused from an insulin cartridge currently in use; the time of the last insulin cartridge replacement and/or infusion set replacement. Some or all of such information is generally stored by an insulin infusion pump. For use as further identification code, the corresponding information may be outputted on a medical device display as optical and/or outputted as optical output as explained before and may be inputted into the remote controller by the remote controller user interface and/or received by a remote controller sensor as explained before. Further, the further identification code or information that is indicative of the further identification code is transmitted from the medical device to the remote controller via the medical device communication interface and the remote controller communication interface, as explained before.

In an embodiment, the medical device includes a continuous glucose measurement device and the time-dependent status is determined from at least one of calibration data, an identification code of a sensor element of the continuous glucose measurement device, and/or glucose measurement results. Calibration data may in particular be or include glucose measurement results that are determined using a further (typically strip-based) glucose measurement device and entered for calibration purposes subsequent to starting use of a fresh sensor element and/or in regular time intervals, such as every 12 hours. The identification code may be for example be or include a lot or serial number of a sensor element that is typically regularly replaced and carries the subcutaneous sensor. Glucose measurement data may be the results of one or more specific glucose measurements that are carried out by the continuous glucose measurement device, e.g., every few minutes. The glucose measurement data may also be derived from glucose measurement results, such as an average of a number of past glucose measurement results. Further, the time dependent status may include the times of past user interactions, the time of one or more past or replacements of the sensor element, the remaining application of a presently used sensor element, or the time of entering glucose measurement results as calibration data.

In an embodiment, determining whether the safety condition is met includes determining whether the medical device and/or the remote controller is at a pre-determined location and/or within a pre-determined area. Similarly, the method may include determining that the medical device and/or the remote controller has entered the pre-determined location and/or pre-determined area. This type of embodiment is based on the assumption that the medical device and the remote controller, respectively the medical system, is under control of an authorized user if they are at the pre-determined location and/or in the pre-determined area. The pre-determined location or area may, for example, be a place of domicile or a workplace. Information regarding one or more pre-determined locations may be stored by the medical device and/or the remote controller. Further, the medical device and/or the remote controller may include a location detector, such as a GPS (Global Positioning System) or Gallileo receiver. In embodiments where the receiver is part of the medical device, information indicative of the position and/or an acknowledgement signal indicating that the medical device is at the pre-determined location and/or within the pre-determined area may be transmitted from the medical device to the remote controller via the remote device communication interface and the remote controller communication interface.

In some embodiments, the further command may be or include an altering of the identification code or resetting of the remote controller to factory settings as explained before. In alternative embodiments, however, the further command is or includes a switching into the unlocked state. For this type of embodiment, the remote controller is automatically switched into the unlocked state as soon as it is determined that the medical device is at the pre-determined location and/or in the pre-determined area. As long as the medical device and/or the remote controller is at the pre-determined location and/or in the pre-determined area, entry of the identification code is not required for accessing the at least one medical device command. Therefore, this type of embodiment is particularly comfortable to use in everyday-life.

In a variant of the before-described type of embodiment, the method further includes determining whether the medical device and/or the remote controller is out of the pre-determined location and/or the pre-determined area, or has left the pre-determined location or area. The method may further include automatically switching the remote controller into the locked state in this case.

In further variants, a wireless receiver, in particular a WLAN (Wireless Local Area Network) receiver may be present. The method may include determining that the medical device respectively the remote controller is at the pre-determined location and/or in the pre-determined area if a pre-determined WLAN signal is received. The WLAN may especially be a WLAN at the user's home, workplace or the like. The WLAN should be uniquely identified. In further variants, another type of wireless receiver, such as a Bluetooth receiver may be present and used in an anlage way.

In an embodiment, determining whether the safety condition is met includes determining whether the medical device and the remote controller are in physical contact or close proximity to each other. For this purpose, mating electric contacts may be provided as part of the medical device and the remote controller, and the mating electric contacts may are brought into galvanic connection. An acknowledgement signal may be exchanged and/or transmitted from the medical device to remote controller, thereby confirming the presence of a physical contact. In an alternative embodiment, corresponding near field communication units (NFCs) are provided as part of the medical device and the remote controller via which the acknowledgement signal is transmitted. The NFCs may have a communication range of, e.g., 0 . . . 5 cm.

In a further variant, close proximity of the medical device and the remote controller is confirmed by transmitting an acoustic output from the medical device to the communication device as explained before. In a further variant, close proximity of the medical device and the remote controller is confirmed by displaying a further identification code on a display of the medical device and receiving the further identification code by an optical detector, in particular a camera, of the remote controller, as explained before.

In a further variant, close proximity of the medical device and the remote controller is determined using the medical device communication unit and the remote controller communication unit. The medical device and the remote controller may, e.g., be assumed to be in close proximity if the signal strength of a radio frequency (RF) signal via which the medical device communication unit and the remote controller communication unit communicate is above a pre-defined signal strength threshold level. In an embodiment, the determination is made by the remote controller based on the signal that is received by the remote controller communication unit from the medical device communication unit.

In an embodiment, step (e) includes carrying out a user interaction with the medical device and transmitting information indicative of the user interaction from the medical device to the remote controller. This type of embodiment may be favourably used if the medical device has a medical device user interface that may be used for providing user input, such as a keyboard, pushbuttons, a touch screen, or the like. In some embodiments, the user interaction may be the entry of a further identification code as explained before. In other embodiments, the user interaction may be any other command that may be entered via the medical user interface. Since communication between the medical device and the remote controller is possible only in a limited communication range of, e.g., about 1 m and further the medical device can be generally assumed to be under direct control of an authorized user, correct transmission of the information indicative of the user interaction from the medical device implies that also the remote controller is under control of the authorized user.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
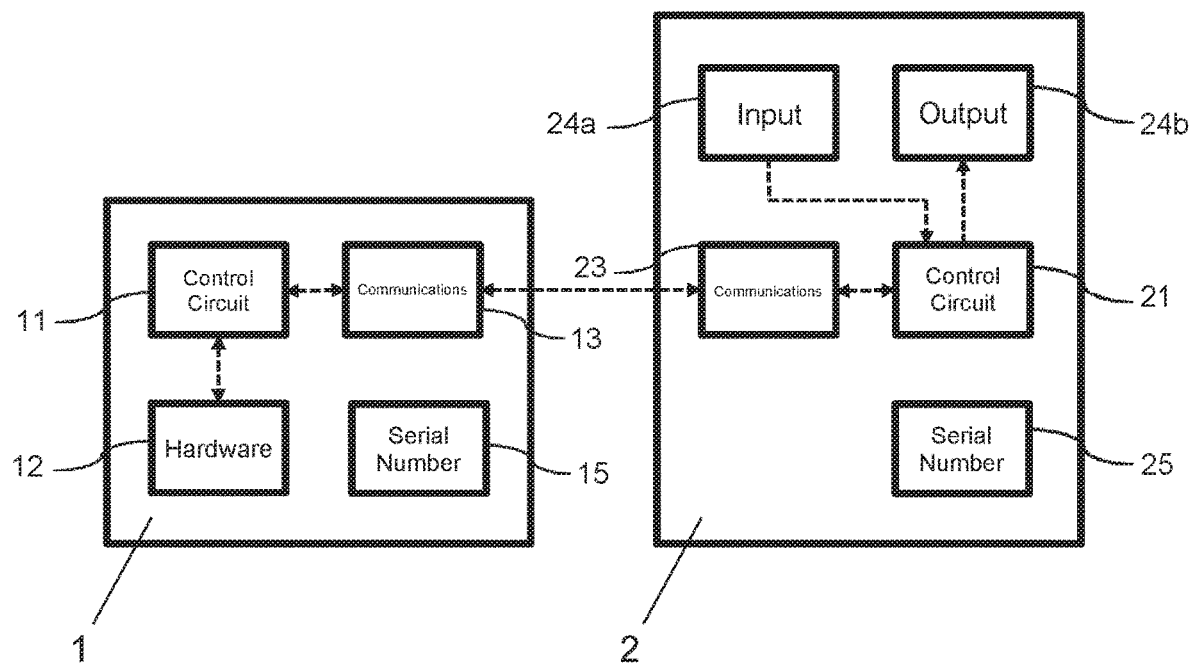
FIG. 1 shows an exemplary medical system in accordance with the present disclosure.

In the following, reference is first made to FIG. 1. FIG. 1 shows a medical system with a medical device 1 and a remote controller 2 in a schematic structural and functional view. Like in further figures, operative couplings between functional units and/or components are indicated by dashed lines.

By way of example, the medical device 1 is an insulin infusion pump that is designed to be carried by a PwD substantially continuously night and day. For this purpose, the medical device 1 is designed and shaped to be carried by the PwD, e g. in a trousers' pocket or with a belt clip, and/or is designed for direct adhesive attachment to the body. In the following, the PwD is assumed to be the authorized user. Alternatively or additionally, however, the authorized user may be another person in charge of controlling and of the medical device 1 such as a parent of a PwD, or a medical professional in a hospital.

In another example, the medical device 1 may be a continuous blood glucose measurement device that is directly attached to the PwD's body for an application time and measure a tissue glucose concentration with a subcutaneous sensor, typically based on an amperometric measurement principle. In a further example, the medical device includes both an insulin infusion pump and a continuous glucose measurement device in a single integral unit or spatially distributed.

The medical device 1 includes a typically microcontroller- and/or microcomputer-based medical device control circuit 11 that controls overall operation of the medical device 1. The medical device 1 further includes a medical device functional unit 12 (hardware) in operative coupling with the medical device control circuit 11. The medical device functional unit 12 realizes the medical functionality of the medical device 1. In the here-assumed case of the medical device 1 being an insulin infusion pump, the medical device functional unit 12 is or includes a metering pump for the metered administration of insulin, in particular basal infusion according to a basal infusion schedule and/or bolus infusion on demand. The medical device functional unit 12 operates under control and supervision of the medical device control circuit 11. The medical device 1 further includes a medical device communication unit 13 (also referred to as communications electronics) as explained further below in more detail. For the medical device 1 being a continuous glucose measurement device, the medical device functional unit 12 may include the measurement circuit and the subcutaneous glucose sensor.

The remote controller 2 typically includes a microcontroller and/or microcomputer-based remote controller control circuit 21 that controls overall operation of the remote controller 2. The remote controller 2 further includes a remote controller user interface 24a, 24b with a remote controller input unit 24a (input) and a remote controller output unit 24b (output). By way of example, the remote controller user interface is realized as a touch screen that incorporates both the remote controller input unit 24a and remote controller output unit 24b, which however, is not essential. The remote controller 2 further includes a remote controller communication unit 23 (also referred to as communications electronics) that is designed for wireless operative communication and data exchange with the medical device communication unit 13, e.g., according to the Bluetooth standard or according to a proprietary communication protocol. Via the user interface 24a, 24b, the user may in particular initiate execution of a medical device command or a set of medical device commands to be executed by medical device 1. By way of example, the medical device command or set of medical device commands includes the administration of an insulin bolus of desired amount, as well as a temporary modification and/or reprogramming of the basal infusion schedule. For the medical device 1 being a continuous glucose measurement device, the medical device command may in particular include commands related to the replacement and exchange of the subcutaneous sensor and calibration, e.g., via additional test-strip based glucose measurements. The remote controller 2 further carries a remote controller serial number 25 that is, e.g., printed on a label or engraved into a housing of the remote controller 2. In the here-assumed example, the remote-controller 2 is a dedicated device that is particularly designed for controlling operation of the medical device 1. Alternatively, however, the remote controller 2 may be a general-purpose device, such as a cell phone, with corresponding functionality for controlling operation of the medical device 1 as part of the remote controller control circuit 21, e.g., as software and/or firmware code.

Figure 2:
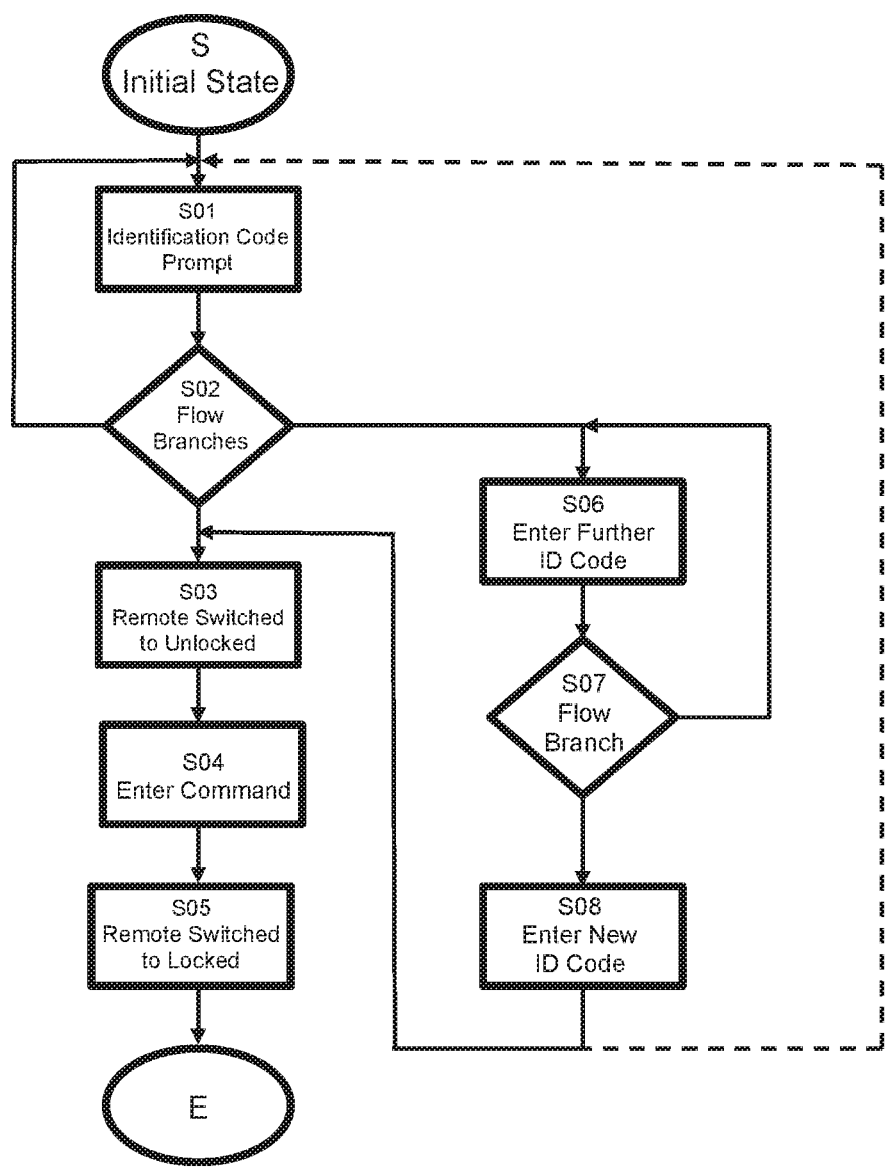
FIG. 2 shows an exemplary operational flow of a method in accordance with the present disclosure.

In the following, reference is additionally made to FIG. 2. FIG. 2 shows an exemplary operational flow of a method for controlling user access to the medical system of FIG. 1 along with further related steps.

The operational flow starts with step S as an initial state. It is assumed that in the initial state S, the remote controller 2 is in the locked state. While not being essential, it is further assumed that the medical device 1 operates in the initial state autonomously under control of the medical device control circuit 11. In particular for an insulin infusion pump, it carries out basal insulin administration in a continuous or substantially continuous way, typically according to a time-varying schedule. The medical device 1 may further carry out any other function such as an earlier-programmed bolus administration. In any case, user access to the medical device command or set of medical device commands is disabled due to the locked state.

In subsequent step S01, the user is prompted by the remote controller 2 to enter, via the remote controller input unit 24a, the identification code or to alternatively indicate that he/she has forgotten the identification code. The transition from S to S01 may, for example, by initiated by a corresponding user operation on the remote controller input unit 24a. In subsequent step S02, the operational flow branches in dependence on the input that is provided in step S01 as follows:

If the identification code is entered incorrectly in step S01, the operational flow returns to step S01. If the identification code is entered correctly in step S01, the operational flow proceeds with step S03, where the remote controller 2 is switched into the unlocked state. In subsequent state S04, the user may enter, via the remote controller input unit 24a, the medical device command or a command from a set of medical device commands. Such medical device command is transmitted, via the remote controller communication unit 23, to the medical device communication unit 13 and is subsequently executed by the medical device 1 under control of the medical device control circuit 11. In an embodiment, the operational flow subsequently proceeds directly to step S05. In another embodiment, the operational flow stays in step S04 and accordingly in the unlocked state, allowing the user to enter further medical device commands. In such embodiment, a transition to step S05 may be triggered by a timeout of no user input. The timeout delay may, e.g., be in a range of 30 sec to 2 min. Other time periods may be used as well. In step S05, the remote controller 2 is switched back into the locked state and the operational flow ends in step E which may correspond to step S.

If indication is provided in step S02 that the identification code is forgotten, the operational flow branches to step S06. In step S06, the user is prompted to enter, via the remote controller input unit 24a, the further identification code. In a variant (not shown), the operational flow automatically branches to step S06 if the identification code is entered incorrectly one or multiple times, e.g., three times, in step S01. In subsequent step S07, the operational flow branches in dependence of the input in step S06. If the further identification code is entered incorrectly, the operational flow returns to step S06 and the further identification code may be re-entered. If the further identification code is entered correctly, the operational flow proceeds with step S08. In step S08 the user is, in an embodiment, prompted to enter a new identification code. In another embodiment, the remote controller 2 and in particular the identification code is reset to a default setting. Subsequently, the operational flow proceeds with step S03 as explained before. In a variant (shown with dashed line), the operational flow proceeds, after step S08, with step S01 where the user is prompted to enter the new identification code. Step S08 is a further command as explained above in the general description.

In this example, the further identification code is formed by a part of the remote controller serial number 25, by the remote controller serial number 25 as a whole, or is derived from the remote controller serial number 25 as explained before in the general description. In another embodiment, a medical device serial number 15 is used instead. In another embodiment, a combination of the medical device serial number 15 and the remote controller serial number 25 is used. In all embodiments, the further identification code is, like the identification code, stored in a memory of the remote controller control circuit 21.

Figure 3:
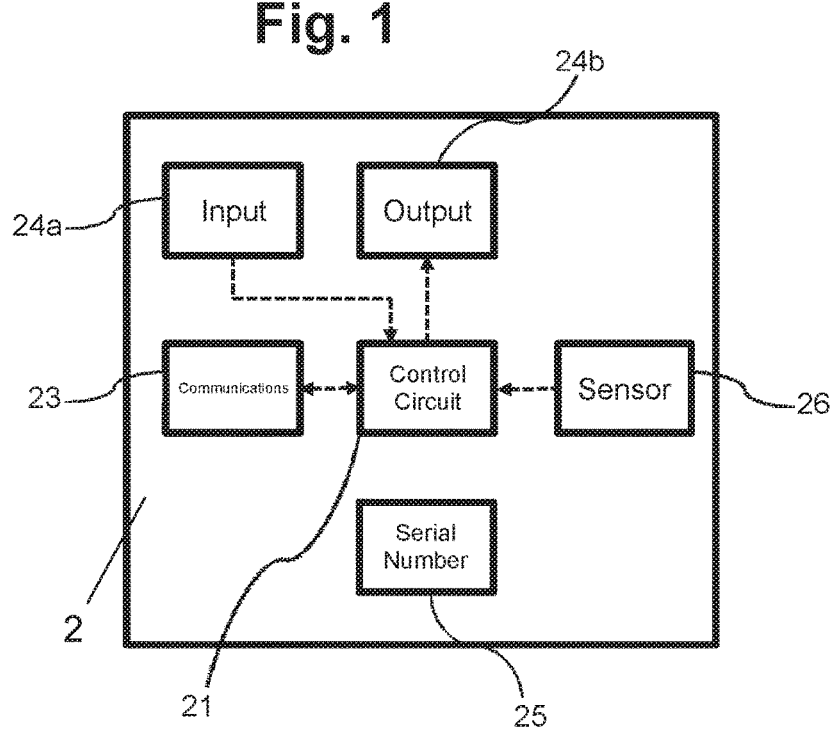
FIG. 3 shows a remote controller of a further exemplary medical system in accordance with the present disclosure.

In the following, reference is additionally made to FIG. 3. FIG. 3 shows another embodiment of the remote controller 2 in a schematic structural and functional view. The remote controller of FIG. 3 may be used instead of the remote controller as shown in FIG. 1. The remote controller 2 of FIG. 3 differs from the remote controller 2 in FIG. 1 in so far as in FIG. 3, the remote controller 2 includes a remote controller sensor 26 in the form of a camera, in operative coupling with the remote controller control circuit 21. Further, the remote controller control circuit 21 is configured to analyze and evaluate information, in particular image information, that is captured by the remote controller sensor 26.

For this type of embodiment, the operational flow is similar to the operational flow as shown in FIG. 2 and discussed before. In this embodiment, however, the user is, in step S06, requested to capture an image of the remote controller serial number 25 and/or the medical device serial number 15 with the remote controller sensor 26. The image is subsequently assessed for correctness by the remote controller control circuit 21. In embodiments where the further identification code is defined, fully or party, by the remote controller serial number 25, the remote controller serial number 25 is favourably provided on an element that may be placed in the viewing field of the camera, e.g., on a removable battery compartment cover.

Figure 4:
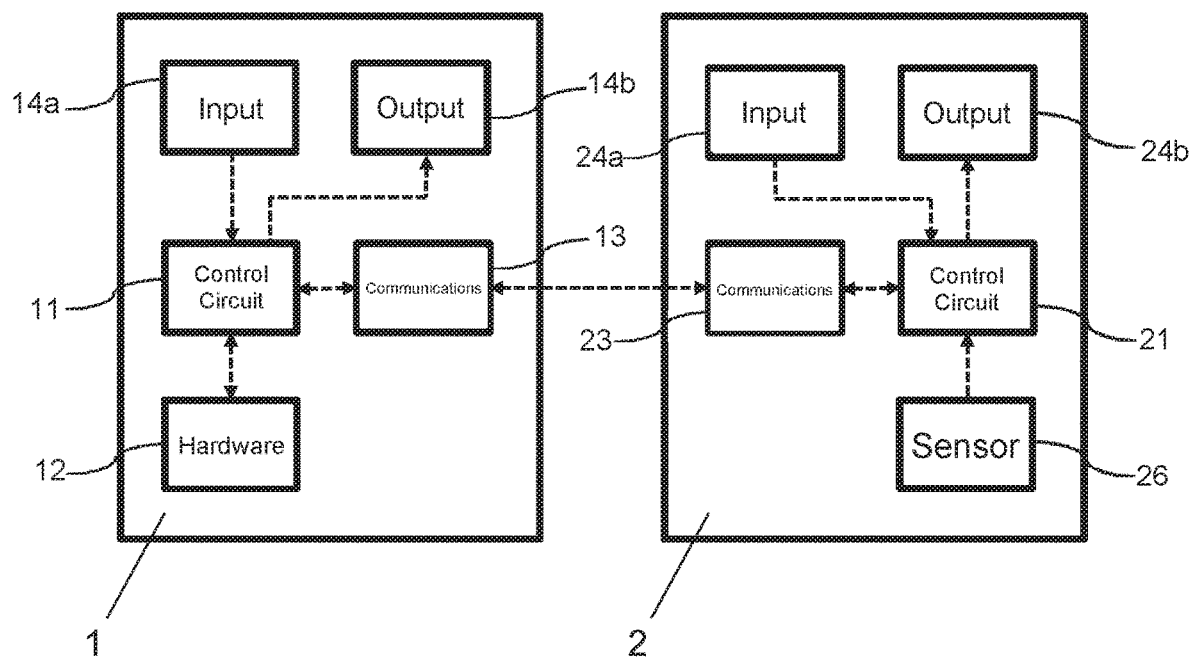
FIG. 4 shows a further exemplary medical system in accordance with the present disclosure.

In the following, reference is additionally made to FIG. 4. FIG. 4 shows a further exemplary embodiment of a medical system that is generally similar to the embodiments of FIG. 1, 3. In the embodiment of FIG. 4, however, the medical device 1 comprises a medical device user interface with a medical device input unit 14a, e.g., one or multiple pushbuttons, and a medical device output unit 14b, e.g., a display. In this embodiment, the medical device output unit 14b is used to display the further identification code.

Figure 5:
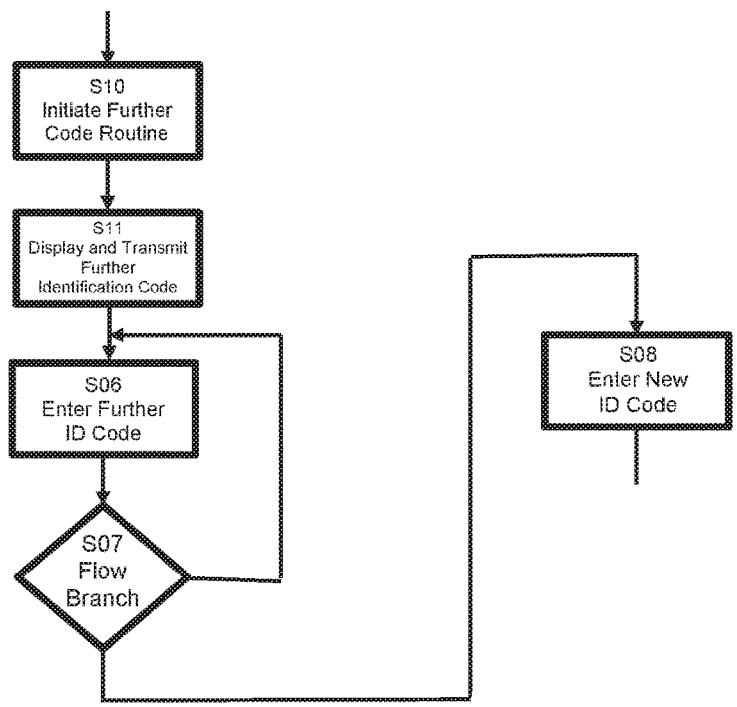
FIG. 5 shows part of an operational flow of a further method in accordance with the present disclosure.

In the following, reference is additionally made to FIG. 5, showing part of an operational flow of a further method for controlling user access to the medical system of FIG. 4.

The sequence shown in FIG. 5 replaces the sequence of steps S06 to S08 of FIG. 2. It is noted, however, that these steps may be present in the embodiment of FIG. 5 as well in a similar or identical way, including the before-described variants.

In step S10, a further identification code routine is initiated on the medical device 1 by the user by way of the medical device user interface, in particular the medical device input unit 14a. The further identification code routine is implemented by the medical device control circuit 11, typically as software or firmware code. In an embodiment, the further identification code is generated as random numeric code or random alphanumeric code. In another embodiment, the remote controller control circuit 11 generates the further identification code based on a time-dependent status of the medical device 1 as explained above in the general description. In subsequent step S11, the further identification code is displayed by the display as medical device output unit 14. Further in step S11, the further identification code is transmitted via the medical device communication unit 13 and the remote controller communication unit 23 from the medical device 1 to the remote controller 2. In this embodiment, the further identification code is not pre-known and stored by the remote controller 2, but is generated by the medical device 1.

In a variant, the medical device output unit 14b is or includes an acoustic or tactile indication device, such as a buzzer, loudspeaker or pager vibrator. Further, the remote controller sensor 26 may include an acoustic or vibration receiver, such as a loudspeaker. For this type of embodiment, the further identification code is emitted by the medical device output unit, in particular, a tactile indication unit 14b and received by the medical device sensor, in particular, an acoustic or vibration receiver 26. For an embodiment where the remote controller sensor 26 is or includes a camera as explained before, a display image of the medical device output unit (display 14b) may be captured by the remote controller sensor, camera 26. These steps may replace the manual inputting of the further identification code via the remote controller input unit 24a.

In a further variant, the further identification code routine is not initiated by a user input on the medical device 1, but instead on the remote controller 2. As part of step S10, a request for generating the further identification code is then transmitted from the remote controller 2 to the medical device 1 via the remote controller communication unit 23 and the medical device communication unit 13. This type of embodiment is particularly favorable where the medical device 1 only has the medical device output unit 14b, e.g., in form of a loudspeaker and/or buzzer as explained before, but has no or a very limited medical device input unit 14a. This is typically the case for medical devices that are designed for direct attachment to the PwDs' body.

Figure 6:
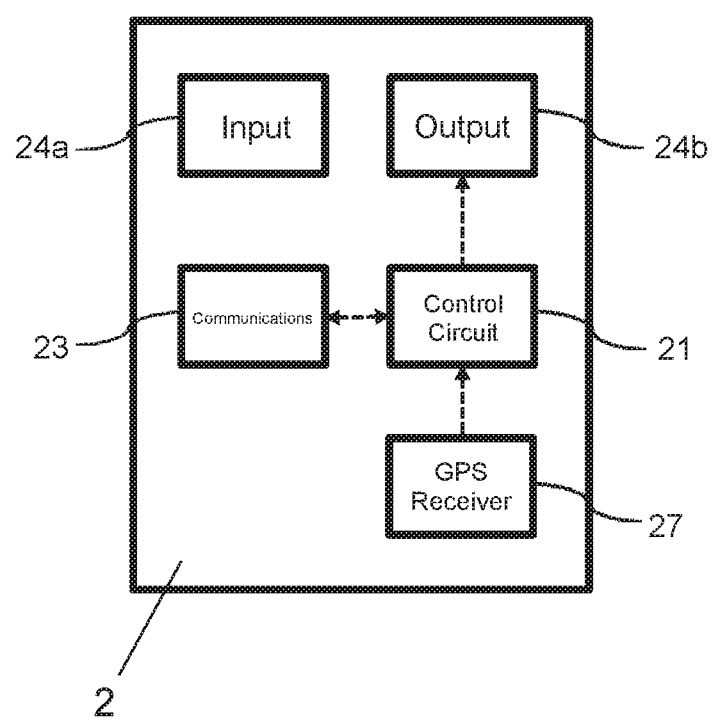
FIG. 6 shows a remote controller of a further exemplary medical system in accordance with the present disclosure.

In the following, reference is additionally made to FIG. 6. FIG. 6 shows another embodiment of the remote controller 2 in a schematic structural and functional view. The remote controller of FIG. 6 may be used instead of the remote controller as shown in FIG. 1. The remote controller 2 of FIG. 6 differs from the remote controller 3 in FIG. 1 in so far as in FIG. 6, the remote controller 2 includes a GPS receiver 27 in operative coupling with the remote controller control circuit 21.

Figure 7:
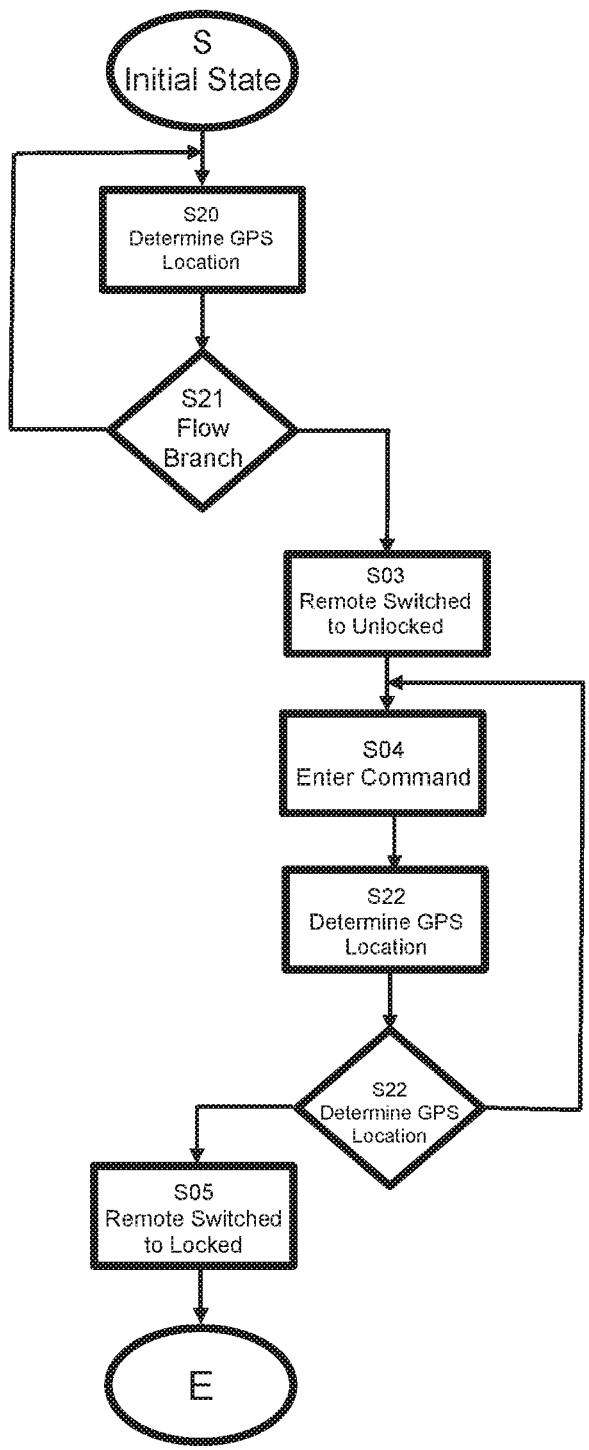
FIG. 7 shows an exemplary operational flow of a further method in accordance with the present disclosure.

In the following, reference is additionally made to FIG. 7. FIG. 7 shows an operational flow of a method for controlling user access to a medical system. The operational flow as shown in FIG. 7 may be carried out with a medical system that includes a remote controller according to FIG. 6.

The operational flow starts in an initial state with step S where the remote controller 2 is in the locked state. In subsequent step S20, the GPS location is determined and compared by the remote controller control circuit 21 with one or more pre-determined locations, e.g., the PwD's home and/or office.

In subsequent step S21, the operational flow branches in dependence of the comparison result. If the determined GPS location does not correspond to a pre-determined location, the operational flow returns to step S20 and the remote controller 2 remains in the locked state.

If the determined GPS location corresponds to a pre-determined location, the operational flow proceeds with steps S03 and S04 as explained before in the context of FIG. 1. The unlocking in step S03 is a further command as explained in the general description. In step S4, a medical device command may be entered and transmitted to the medical device 1 as explained before. If no medical device command is entered, no action is carried out in step S04.

In subsequent step S22, the GPS location is determined like in step S20 as explained before and the operational flow branches in subsequent step S22 in dependence of the result like in step S21. If the GPS location corresponds to a pre-determined location, the operational flow returns to step S04 with the remote controller 2 remaining in the unlocked state. If the GPS location does not correspond to a pre-determined location, the operational flow proceeds with step S05 where the remote controller 2 is switched into the locked state and the operational flow ends.

It is noted that the operational flow of FIG. 7 only shows the controlling of user access in dependence of the GPS location. In the locked state, switching into the unlocked state is further possible by entering the identification code as explained before in the context of FIG. 2. Further, a command that may be provided in step S04 is a changing of the identification code. For this type of embodiment, the remote controller 2 is accordingly in the unlocked state and all commands are available whenever the remote controller 2 is at a pre-determined location. At such pre-determined location, the identification code may also be changed without requiring the entry of a further identification code.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS

1 medical device (insulin infusion pump)
11 medical device control circuit
12 medical device functional unit
13 medical device communication unit
14a medical device user interface (input unit)
14b medical device user interface (output unit)
15 medical device serial number
2 remote controller
21 remote controller control circuit
23 remote controller communication unit
24a remote controller user interface (input unit)
24b remote controller user interface (output unit)
25 remote controller serial number
26 remote controller sensor/camera
27 GPS receiver

What is claimed is:

1. A method for controlling user access to a medical system, comprising:
   a) providing an extracorporeal body-wearable medical device including an insulin infusion pump and/or a continuous glucose monitor, the body-wearable medical device including a medical device communication unit;
   b) providing a remote controller as a separate device from the body-wearable medical device, the remote controller having a user interface and a remote controller communication unit configured for data exchange with the medical device communication unit, the remote controller further configured for entering, via the user interface, at least one command for execution by the body-wearable medical device;
   c) controlling the remote controller to be in a locked state, wherein, in the locked state, entering of the at least one medical device command and execution of a further command are disabled;
   d) from the locked state, requesting entry of an identification code via the remote controller user interface;
   e) when the correct identification code is entered in step (d), switching the remote controller into an unlocked state, wherein, in the unlocked state, entering of the at least one medical device command is enabled;
   f) when the correct identification code is not entered in step (d), determining by the medical system whether a safety condition is met and, when the medical system determines that the safety condition is met, enabling execution of the further command, wherein the safety condition requires an authorized user to be in control of the medical system.

2. The method according to claim 1, comprising receiving a user input indicative of the identification code being unavailable, and carrying out step (f).

3. The method according to claim 1, wherein the further command includes switching the medical device into the unlocked state.

4. The method according to claim 1, wherein the further command is an altering of the identification code and/or resetting of the remote controller to factory settings.

5. The method according to claim 1, wherein step (f) includes inputting a further identification code and determining whether the safety condition is met comprises determining whether the further identification code is inputted correctly.

6. The method according to claim 5, wherein the remote controller includes a sensor and step (f) comprises determining whether the further identification code is recognized by the sensor.

7. The method according to either of claim 5, wherein the further identification code is provided on or by the medical device.

8. The method according to claim 7, wherein the method includes transmitting information indicative of the further identification code from the medical device to the remote controller via the medical device communication unit and the remote controller communication unit.

9. The method according to claim 7, wherein the further identification code is or is derived from a time-dependent status of the medical device.

10. The method according to claim 9, wherein the medical device includes an insulin infusion pump and the time-dependent status is determined by past insulin infusion by the medical device.

11. The method according to claim 9, wherein the medical device includes a continuous glucose measurement device and the time-dependent status is determined from at least one of calibration data, an identification code of a sensor element of the continuous glucose measurement device, and/or glucose measurement data.

12. The method according to claim 5, wherein the further identification code is provided on or by the remote controller.

13. The method according to claim 1, wherein determining whether the safety condition is met includes determining whether the medical device and/or the remote controller is at a pre-determined location and/or within a pre-determined area.

14. The method according to claim 1, wherein determining whether the safety condition is met includes determining whether the medical device and the remote controller are in physical contact or in close proximity to each other.

15. The method according to claim 1, wherein step (f) includes carrying out a user interaction with the medical device and transmitting information indicative of the user interaction from the medical device to the remote controller.

* * * * *